United States Patent
Karandikar et al.

(10) Patent No.: US 9,381,269 B2
(45) Date of Patent: Jul. 5, 2016

(54) BIOSORBABLE WOUND TREATMENT DEVICE, PROCESS FOR MAKING, AND METHOD OF USING THE SAME

(75) Inventors: Bhalchandra M. Karandikar, Beaverton, OR (US); Sophie Truc Lam, Beaverton, OR (US)

(73) Assignee: Avent, Inc., Alpharetta, GA (US)

( * ) Notice: Subject to any disclaimer, the term of this patent is extended or adjusted under 35 U.S.C. 154(b) by 1036 days.

(21) Appl. No.: 13/428,370

(22) Filed: Mar. 23, 2012

(65) Prior Publication Data

US 2012/0265124 A1   Oct. 18, 2012

Related U.S. Application Data

(60) Provisional application No. 61/474,900, filed on Apr. 13, 2011.

(51) Int. Cl.
| | | |
|---|---|---|
| *A61L 15/42* | (2006.01) | |
| *A61L 15/44* | (2006.01) | |
| *A61L 15/60* | (2006.01) | |

(52) U.S. Cl.
CPC .............. *A61L 15/425* (2013.01); *A61L 15/44* (2013.01); *A61L 15/60* (2013.01); *A61L 2300/11* (2013.01)

(58) Field of Classification Search
CPC ....... A61L 15/60; A61L 15/44; A61L 15/425; A61L 2300/11; C08L 3/04; C08L 5/08; C08L 5/04; A61K 8/042
See application file for complete search history.

(56) References Cited

U.S. PATENT DOCUMENTS

| | | |
|---|---|---|
| 4,124,705 A | 11/1978 | Rothman et al. |
| 4,582,865 A | 4/1986 | Balazs et al. |
| 5,086,620 A | 2/1992 | Spears |
| 5,206,341 A | 4/1993 | Ibay et al. |
| 5,407,685 A | 4/1995 | Malchesky et al. |
| 5,635,609 A | 6/1997 | Levy et al. |

(Continued)

FOREIGN PATENT DOCUMENTS

| | | |
|---|---|---|
| WO | WO 2004/108176 A1 | 12/2004 |
| WO | WO 2006/015317 A2 | 2/2006 |
| WO | WO 2006/026026 A2 | 3/2006 |

OTHER PUBLICATIONS

Cha, Chaenyung et al., "Integrative Design of a Poly(ethylene glycol)-Poly(propylene glycol)-Alginate Hydrogel to Control Three Dimensional Biomineralization," Biomaterials, vol. 32, No. 11, Dec. 26, 2010, pp. 2695-2703.

(Continued)

*Primary Examiner* — Nathan R Price
*Assistant Examiner* — Melissa A Snyder
(74) *Attorney, Agent, or Firm* — Dority & Manning, P.A.

(57) ABSTRACT

A biosorbable oxygen-delivery wound treatment device that includes a biosorbable matrix for delivering oxygen. The biosorbable matrix includes a water swellable, cross-linked biosorbable polymer network. A plurality of gas-permeable, elastic, closed cells is defined by the cross-linked biosorbable polymer network. According to the invention, these closed cells may be produced from a reaction between a catalyst and a second reactant. Deliverable oxygen is contained within the elastic closed cells such that when the device is used to treat a wound, oxygen is delivered from the closed cells. A process for making a biosorbable oxygen-delivery wound treatment device that includes a biosorbable matrix for delivering oxygen as well as a method of using an oxygen-delivery wound treatment device is disclosed.

17 Claims, 2 Drawing Sheets

(56) References Cited

U.S. PATENT DOCUMENTS

| | | |
|---|---|---|
| 5,736,582 A | 4/1998 | Devillez |
| 5,792,090 A | 8/1998 | Ladin |
| 5,855,570 A | 1/1999 | Scherson et al. |
| 5,928,174 A | 7/1999 | Gibbins |
| 7,160,553 B2 * | 1/2007 | Gibbins ............... A61K 33/40 424/443 |
| 8,679,523 B2 | 3/2014 | Gibbins et al. |
| 2005/0159695 A1 * | 7/2005 | Cullen ................ A61L 15/28 602/48 |

OTHER PUBLICATIONS

Suhaila B. Mohamed et al., Ability of Various Proteins to Form Thermostable Gels with Propylene Glycol Algiate, Food Chemistry, vol. 13, 1984, 15 pages.

J.N. Petersen et al., Size Changes Associated with Metal Adsorption onto Modified Bone Gelatin Beads, Biotechnology and Bioengineering, vol. 38, 1991, 6 pages.

* cited by examiner

BIOSORBABLE WOUND TREATMENT DEVICE, PROCESS FOR MAKING, AND METHOD OF USING THE SAME

This application claims the benefit of priority from U.S. Provisional Application No. 61/474,900 filed on Apr. 13, 2011, the contents of which are incorporated herein by reference.

FIELD OF THE INVENTION

The present invention relates to generally to the field of wound treatment devices for the delivery of gases and other agents to compromised tissues.

BACKGROUND

Damage or destruction of the blood supply to a region of living tissue quickly leads to compromised tissue. One of the critical functions of an adequate blood supply is the provision of dissolved gases to the site, such as oxygen. For example, wounds to bodily tissues are accompanied by damage or destruction of the natural blood supply that transports oxygen and nutrients that are necessary to support the healing process. Measurements have shown that the tissue oxygen tension within the wound and surrounding damaged tissues is substantially lower than the normal blood vascular oxygen tension. Whereas the blood vascular oxygen level of 80 to 100 mm Hg is considered normal, the wound environment may have as little as 3 to 30 mm Hg of oxygen. Research has shown that a level of 30 mm Hg or less is insufficient to support the processes of wound repair.

Oxygen has been shown to have therapeutic effect in healing of wounds and in preventing growth of anaerobic bacteria etc. While oxygen may be available from air for direct dissolution into wound fluids, availability of topically dissolved oxygen is preferred as it raises oxygen tension to desired levels more quickly, thus accelerating its benefits in wound healing.

Many approaches have been used in an effort to increase the amount of oxygen delivered to compromised tissues. For example, U.S. Pat. No. 5,407,685 describes a device for generating oxygen when the device was applied to a wound. The device disclosed is a bilayered device where each layer contains a reactant that mixes and generates oxygen once exudate or other bodily-derived material activates the reaction. U.S. Pat. No. 5,736,582 describes the generation of oxygen from hydrogen peroxide for release at or near the skin surface. U.S. Pat. No. 5,855,570 similarly uses an electrochemical reaction to convert oxygen in air to a peroxide or other reactive form of oxygen for delivery to the wound environment. U.S. Pat. No. 5,792,090 uses a reservoir that contained hydrogen peroxide and a catalyst in a device in contact with the wound, such as a hydrogel or polymeric foam. Another approach was disclosed in U.S. Pat. No. 5,086,620 in which pure gaseous oxygen was dispersed by sonic energy into a liquid matrix that was then solidified by cooling to encapsulate the oxygen in minute bubbles.

These devices represent improvements in the delivery of topical oxygen to the wound environment over conventional hyperbaric chambers. However, each carries significant limitations that have restricted the broad adaptation of the technology of topical oxygenation for care of compromised tissues. Previously described devices do not have a known concentration of oxygen and cannot function independently of atmospheric pressures or temperature to achieve effective oxygen distribution. In addition, the dependence upon activation by body-derived agents is unpredictable so as to make such devices impractical. Other devices are expensive to produce and require specialized equipment. Such devices cannot be used in the production of cold set polymers that are often used for the construction of medical devices used for compromised tissue care.

One particularly useful approach to delivering oxygen to a wound is described in U.S. Pat. No. 7,160,553 for "Matrix for Oxygen Delivery to Compromised Tissues", issued Jan. 9, 2009 to Gibbins et al. That patent describes a closed cell oxygen-containing foam dressing based on polyacrylamide. The closed cell oxygen foam dressing is biocompatible and laboratory tests have shown the dressing is able to increase oxygen tension in saline as high as 200 mm Hg. The foam dressing has high capacity for fluid absorption (up to 10 grams fluid per gram of foam) and has no adverse cytotoxicity. The foam dressing is suited for application in surface wounds for sustained delivery of topically dissolved oxygen for 72 hours. While the closed cell oxygen foam dressing is biocompatible, it is not biosorbable. (i.e., it is not suitable for use inside the human body).

In a variety of surgical situations, especially those involving internal surgeries, there is a need for a sheet dressing that may act as a spacer, help heal surgical incisions faster by supplying topically dissolved oxygen and doing away with the need for removal of dressing from the surgical site due to its intrinsic biosorbable property. There are biosorbable collagen sponges and some polyurethane base biosorbable dressings known in published literature. However, none are able to provide topically dissolved oxygen in addition to be biocompatible and biosorbable.

The Gibbins et al. patent describes the use of gelatin, a biodegradable material, for making a non-polyacrylate based oxygen foam dressing using a sodium carbonate-hydrogen peroxide system which resulted in a pliable foam material with oxygen gas trapped in bubbles within the dressing. However, such a dressing is not cross-linked (unlike its polyacrylate counterpart) and would lack wet strength. Such a deficiency makes handling of the dressing during manufacturing and in use difficult and impractical.

The wet strength of the gelatin gel sheets could be improved by cross-linking them with the help of glutaraldehyde or formaldehyde. While these two reagents are the most commonly used in gelatin cross-linking, they are unsuitable for making cross-linked gelatin biosorbable oxygen foam dressings because they are toxic. Any residue of these chemicals in the dressings is highly undesirable.

Accordingly, there is a need for a biosorbable closed cell oxygen foam that has wet strength and is practical to manufacture and handle. There is also a need for a practical and economical method of manufacturing such a biosorbable closed cell oxygen foam having wet strength properties. A need also exists for a sheet dressing that may act as a spacer, help heal surgical incisions faster by supplying topically dissolved oxygen and doing away with the need for removal of the dressing from the surgical site. Moreover, there is a need for methods of using a sheet dressing as a spacer to help heal surgical incisions faster by supplying topically dissolved oxygen and doing away with the need for removal of the dressing from the surgical site. Methods and compositions are needed that can provide oxygen to a surgical site and delivery of active agents with the need for removal of a dressing from the surgical site.

SUMMARY

In response to the difficulties and problems discussed herein, the present invention provides a biosorbable oxygen-delivery wound treatment device that includes a biosorbable matrix for delivering oxygen. The biosorbable matrix includes a water swellable, cross-linked biosorbable polymer network. A plurality of gas-permeable, elastic, closed cells is defined by the cross-linked biosorbable polymer network. According to the invention, these closed cells may be produced from a reaction between a catalyst and a second reactant. Deliverable oxygen is contained within the elastic closed cells such that when the device is used to treat a wound, oxygen is delivered from the closed cells.

The biosorbable polymer network is formed from a biosorbable polymer that can be cross-linked into a water-swellable polymer network. The cross-linked polymer network should flexible such that it can define elastic, closed cells that are also gas permeable. Exemplary cross-linkable biosorbable polymers include hyaluronic acid and hyaluronic acid derivatives, alginic acid and alginic acid derivatives, collagen, chitosan, chitin, starch derivatives, natural gums, citric acid based polymers, lactic acid and glycolic acid based polymers, poly(aspartates), poly(orthoesters), poly(phosphazenes), poly(anhydrides), poly(phosphoesters), polyalkylene glycol based polymers, and combinations thereof.

According to an aspect of the invention, the biosorbable polymer network can be formed from propylene glycol alginate and gelatin. The ratio of these ingredients may be varied to change the properties of the resulting polymer network.

The second reactant is desirably hydrogen peroxide. However, other peroxides, including, but not limited to, urea peroxide, sodium peroxide and other peroxy compounds can be used provided they leave no residue that would be inconsistent with bioabsorption. The present invention contemplates use of components that can generate a gaseous element within the matrix and that are safe and effective for use. For example, an acid catalyst can be incorporated in the matrix followed by perfusion of the matrix with a carbonate to generate carbon dioxide gas within the matrix. Such materials are then used to buffer solutions or environments.

The catalyst may be sodium carbonate. However, other catalysts, for example, salts of alkali metals and alkali earth metals may be used provided they are consistent with the product being biosorbable. In addition, more than one catalyst may be used. For instance, one catalyst may be derived from a group consisting of salts of alkali metals and alkali earth metals and the second catalyst may include, but are not limited to, organic and inorganic chemicals such as cupric chloride, ferric chloride, manganese oxide, sodium iodide and their equivalents. Other catalysts, include, but are not limited to enzymes such as lactoperoxidase and catalase.

The biosorbable matrix may include a non-gellable polysaccharide. The biosorbable matrix may further include a plasticizer. The biosorbable matrix may further include a hydration control agent. It is contemplated that the biosorbable matrix may further include a water loss control agent. To decrease the permeability of the matrix, water loss control agents may be applied to a surface of the device. Application of water loss control agents may be useful since a decrease in the permeability of the device controls the loss of fluids. The preferred water loss control agent is petrolatum, however, other water loss control agents such as glycolipids, ceramides, free fatty acids, cholesterol, triglycerides, sterylesters, cholesteryl sulfate, linoleic ethyl ester and silicone oil may also be used. Additionally, the compositions and devices may have an impermeable sheet covering one or more surfaces to aid in control of moisture.

According to an aspect of the invention, the biosorbable matrix may further include active agent. The active agents may aid and improve the wound healing process, and may include gases, anti-microbial agents, including but not limited to, anti-fungal agents, anti-bacterial agents, anti-viral agents and anti-parasitic agents, mycoplasma treatments, growth factors, proteins, nucleic acids, angiogenic factors, anesthetics, mucopolysaccharides, metals and other wound healing agents.

The devices of the present invention may take many physical forms, depending on uses of the devices. A preferred shape is a gel sheet that can be cut or molded into any two dimensional shape. Other preferred embodiments are primarily constructed of thin strands of matrix suitable for placement into the wound bed or cavity.

The present invention encompasses a process for making a biosorbable oxygen-delivery wound treatment device that includes a biosorbable matrix for delivering oxygen. The process generally involves at least the steps of: providing a gelling mixture of at least one cross-linkable biosorbable polymer and a catalyst; cross-linking the biosorbable polymer of the gelling mixture to form a water swellable, cross-linked biosorbable polymer network; drying the gelling mixture to a gel sheet; adding a second reactant to the gel sheet; and generating a plurality of closed cells containing oxygen in the gel sheet by reacting the catalyst and the second reactant.

In an aspect of the invention, the at least one cross-linkable biosorbable polymer of the gelling mixture may be propylene glycol alginate and gelatin. In another aspect of the invention, the cross-linking may be carried out by generating alkaline conditions in the gelling mixture. For example, the alkaline conditions can be generated by addition of sodium carbonate or other alkali and alkali earth compounds provided they are consistent with the product being biosorbable.

In the process of the present invention, the second reactant can be a peroxide such as hydrogen peroxide and the catalyst may be a carbonate such as sodium carbonate. It is contemplated that the method may further include the step of incorporating an active agent.

The present invention also encompasses a method of using an oxygen-delivery wound treatment device. The method of using an oxygen-delivery wound treatment device generally includes the following steps: placing a biosorbable oxygen-delivery wound treatment device composed of an above-described biosorbable matrix for delivering oxygen in a wound or surgical incision site in a mammal; delivering oxygen from the closed cells to the wound or surgical incision site; and allowing the biosorbable oxygen-delivery wound treatment device in the wound or surgical incision site to be resorbed by the mammal.

Other objects, advantages and applications of the present disclosure will be made clear by the following detailed description.

DETAILED DESCRIPTION

Figure 1:
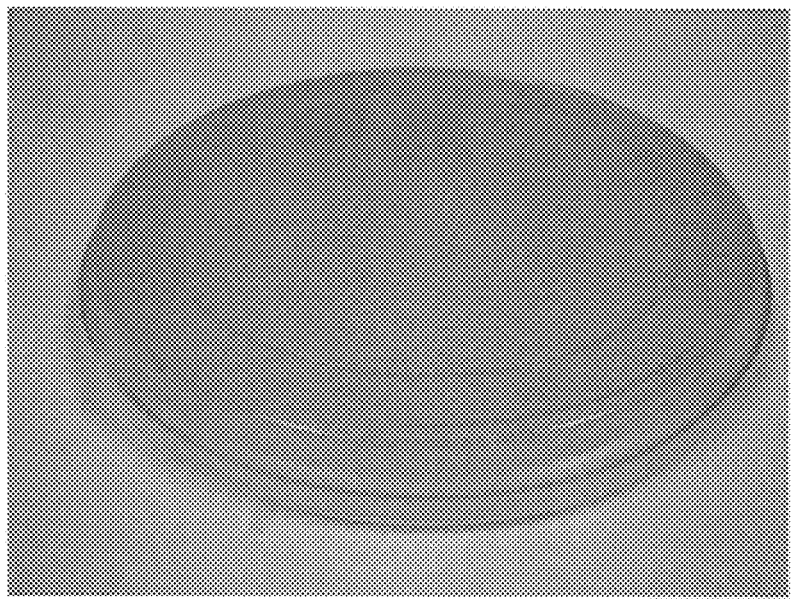
FIG. 1 is photograph illustrating an exemplary swellable, cross-linked biosorbable polymer matrix after dehydration but prior to formation of closed cells containing a gas.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure. As used herein, the terms "bioresorbable", "resorbably", "bioabsorbable" and "biosorbable" are used interchangeably and refer to materials that can be broken down by the body and that do not require mechanical removal. For example, bioresorbable materials may be degraded in a biologic environment, and their breakdown products are incorporated into normal cellular physiologic and biochemical processes. Such materials must be well tolerated with no immunogenic or mutagenic tendency.

The present invention provides a biosorbable oxygen-delivery wound treatment device that includes a biosorbable matrix for delivering oxygen. The biosorbable matrix includes a water swellable, cross-linked biosorbable polymer network. A plurality of gas-permeable, elastic, closed cells is defined by the cross-linked biosorbable polymer network. According to the invention, these closed cells may be produced from a reaction between a catalyst and a second reactant. Deliverable oxygen is contained within the elastic closed cells such that when the device is used to treat a wound, oxygen is delivered from the closed cells.

The biosorbable polymer network is formed from a biosorbable polymer that can be cross-linked into a water-swellable polymer network. The cross-linked polymer network should be flexible such that it can define elastic, closed cells that are also gas permeable. While a variety of biopolymers (i.e., a polymer found in nature and include, but are not limited to, starches, proteins, peptides) either naturally derived or synthetic may be used to prepare biosorbable polymer network, biopolymers that are cross-linkable and biosorbable in vivo are preferred. Exemplary biopolymers include, but are not limited to, hyaluronic acid and its derivatives (see U.S. Pat. No. 4,582,865, the entire contents of which are incorporated herein by reference), alginic acid and its derivatives, collagen, chitosan, chitin, starch derivatives (see U.S. Pat. No. 4,124,705 the entire contents of which are incorporated herein by reference), gums such guar gum, xanthan gum (see U.S. Pat. No. 4,582,865, the entire contents of which are incorporated herein by reference), citric acid based polymers (Gyawali D et. al., BioMaterials (2010), doi: 10.1016/j.biomaterials. 2010.08022), lactic acid and glycolic acid based polymers (see U.S. Pat. No. 5,206,341, the entire contents of which and references cited therein are incorporated herein by reference), poly(aspartates, See Journal of Industrial & Engineering Chemistry, Vol. 6 (#4), pp 276-79, 2010), poly(orthoesters), poly(phosphazenes), poly(anhydrides), poly(phosphoesters) and polyalkylene glycol based polymers.

According to an aspect of the invention, the cross-linked biosorbable polymer network can be formed from propylene glycol alginate and gelatin (i.e., a mixture of proteins obtained by hydrolysis of collagen). These components can be cross-linked under alkaline conditions (e.g., pH>8) to insoluble matter that is water-swellable. Sodium carbonate may be used to increase alkalinity. The ratio of these ingredients may be varied to change the properties of the resulting polymer network. For example, the weight ratio of gelatin to propylene glycol alginate may range from about 1.5:1 to about 6:1. More desirably, the weight ratio of gelatin to propylene glycol alginate may range from about 2:1 to about 5:1. Still more desirably, the weight ratio of gelatin to propylene glycol alginate may range from about 2.5:1 to about 3.5:1. Gelatin source may be a mammal or fish. It may be an output of either an acid or alkali process with different bloom strengths. Though, bovine gelatin is preferred.

The second reactant is desirably hydrogen peroxide. However, other peroxides, including, but not limited to, urea peroxide, sodium peroxide and other peroxy compounds can be used provided they leave no residue that would be inconsistent with bioabsorption. The present invention contemplates use of components that can generate a gaseous element within the matrix and that are safe and effective for use. For example, an acid catalyst can be incorporated in the matrix followed by perfusion of the matrix with a carbonate to generate carbon dioxide gas within the matrix. Such materials are then used to buffer solutions or environments.

The catalyst may be sodium carbonate. However, other catalysts such as other alkali and alkali earth compounds may be used provided they are consistent with the product being biosorbable. In addition, more than one catalyst may be used. For instance, one catalyst may be derived from a group consisting of salts of alkali metals and alkali earth metals and the second catalyst may include, but are not limited to, organic and inorganic chemicals such as cupric chloride, ferric chloride, manganese oxide, sodium iodide and their equivalents. Other catalysts, include, but are not limited to enzymes such as lactoperoxidase and catalase.

The biosorbable matrix may include a non-gellable polysaccharide. Examples of suitable non-gellable polysaccharides include guar gum, guar gum, lucerne, fenugreek, honey locust bean gum, white clover bean gum, or carob locust bean gum. The biosorbable matrix may further include a plasticizer. The plasticizers may be glycerol and/or water, however, propylene glycol and/or butanol and combinations thereof may also be used. If glycerol is used, a range of between approximately 0.25 to 25% w/w, preferably between 0.5 to 12% w/w. The biosorbable matrix may further include a hydration control agent. The hydration control agent may be an isopropyl alcohol; however, ethanol, glycerol, butanol, and/or propylene glycol and combinations thereof may also be used. A range of isopropyl alcohol of between approximately 0.05 to 5% w/w, preferably between approximately 0.1 to 2.5% w/w and most preferably between approximately 0.25 to 1% w/w is generally sufficient. For example, when the cross-linked biosorbable polymer network is formed from propylene glycol alginate and gelatin under alkaline conditions (e.g., pH>8), the degree of water-swelling may be increased by adding a non-gellable polysaccharide such as guar gum and by adding a hydration control agent such as glycerol. By making the cross-linked biosorbable polymer network sufficiently water-swellable, the second reactant (e.g., hydrogen peroxide) may be absorbed into the cross-linked biosorbable polymer network. To ascertain quantitatively the swellability of biosorbable matrix by aqueous fluids, it is important to measure its hydration capacity, expressed as "water absorption capacity" at 25 degrees Centigrade after an immersion or soak time in distilled water after 3 to 4 hours. Useful levels of water absorption capacity may range from about 2 to about 8 grams of water per gram of biosorbable polymer network. For example, the level of water absorption capacity may range from about 3 to about 7 grams of water per gram of biosorbable polymer network. As another example, the level of water absorption capacity may range from about 4 to about 6 grams of water per gram of biosorbable polymer network.

It is contemplated that the biosorbable matrix may further include a water loss control agent. To decrease the permeability of the matrix, water loss control agents may be applied to a surface of the device. Application of water loss control agents may be useful since a decrease in the permeability of the device controls the loss of fluids. The preferred water loss control agent is petrolatum, however, other water loss control agents such as glycolipids, ceramides, free fatty acids, cholesterol, triglycerides, sterylesters, cholesteryl sulfate, linoleic ethyl ester and silicone oil may also be used. Additionally, the compositions and devices may have an impermeable sheet covering one or more surfaces to aid in control of moisture.

The devices of the present invention may take many physical forms, depending on uses of the devices. These devices may be left in place and are then resorbed by the body, instead of being removed. A preferred shape is a gel sheet that can be cut or molded into any two dimensional shape. Other preferred embodiments are primarily constructed of thin strands of matrix suitable for placement into the wound bed or cavity. The devices may be placed in their entirety into a wound, placed in combination with additional bundles of the same design into the wound, or cut through the bridge between strands to reduce the size or number of strands present in the wound. Exemplary structures include, but are not limited to, those described in U.S. Pat. No. 5,928,174 for "Wound Dressing Device" issued Jul. 27, 1999 to Gibbins.

According to an aspect of the invention, the biosorbable matrix may further include active agents. The active agents may aid and improve the wound healing process, and may include gases, anti-microbial agents, including but not limited to, preservatives, anti-fungal agents, anti-bacterial agents, anti-viral agents and anti-parasitic agents, mycoplasma treatments, growth factors, proteins, nucleic acids, angiogenic factors, anesthetics, mucopolysaccharides, metals and other wound healing agents.

Active agents include, but are not limited to, gases, such as oxygen, nitrogen, carbon dioxide, and noble gases, pharmaceuticals, chemotherapeutic agents, herbicides, growth inhibitors, anti-fungal agents, anti-bacterial agents, anti-viral agents and anti-parasitic agents, mycoplasma treatments, growth factors, proteins, nucleic acids, angiogenic factors, anesthetics, mucopolysaccharides, metals, wound healing agents, growth promoters, indicators of change in the environment, enzymes, nutrients, vitamins, minerals, carbohydrates, fats, fatty acids, nucleosides, nucleotides, amino acids, sera, antibodies and fragments thereof, lectins, immune stimulants, immune suppressors, coagulation factors, neurochemicals, cellular receptors, antigens, adjuvants, radioactive materials, and other agents that effect cells or cellular processes.

Examples of anti-microbial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate. Additional silver compounds that may be used are disclosed in the PCT Applications Serial Nos. PCT/US2005/27260 and PCT/US2005/27261 that are incorporated herein in the entirety by reference.

Growth factor agents that may be incorporated into compositions and devices of the present invention include, but are not limited to, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β), interleukin-8 (IL-8); granulocyte-macrophage colony stimulating factor (GM-CSF); the interleukins, and the interferons.

Other agents that may be incorporated into compositions and devices of the present invention are acid mucopolysaccharides including, but are not limited to, heparin, heparin sulfate, heparinoids, dermatitin sulfate, pentosan polysulfate, chondroitin sulfate, hyaluronic acid, cellulose, agarose, chitin, dextran, carrageenan, linoleic acid, and allantoin.

Proteins that may be especially useful in the treatment of compromised tissues, such as wounds, include, but are not limited to, collagen, cross-linked collagen, fibronectin, laminin, elastin, and cross-linked elastin or combinations and fragments thereof. Adjuvants, or compositions that boost an immune response, may also be used in conjunction with the wound dressing devices of the present invention.

Other wound healing agents that are contemplated in the present invention include, but are not limited to, metals. Metals such as zinc and silver have long been known to provide excellent treatment for wounds. Delivery of such agents, by the methods and compositions of the present invention, provide a new dimension of care for wounds.

The active agents can be incorporated into these devices so that the incorporated agents may be released over a period of time, and the rate of release can be controlled by the amount of cross-linking of the polymers of the matrices that in turn affects the erosion of the matrix in vivo and hence the biosorption rate. In this way, the present invention retains its ability to affect the local environment, kill or inhibit microorganisms, boost the immune response, exert other alterations of physiological function and provide active agents over an extended period of time.

The active agents may be incorporated directly into microcavities of the matrix of the wound dressing devices. The agents may be incorporated by absorption of agents by the matrix, and preferably by incorporation during the polymerization of the matrix. It is theorized that the release of the active agents may be controlled via manipulation of concentration parameters, movement of water through the matrix, the degree of cross linking in the matrix and erosion rate of the matrix in vivo.

The present invention encompasses a process for making a biosorbable oxygen-delivery wound treatment device that includes a biosorbable matrix for delivering oxygen. A feature of the matrices of the present invention is the formation of the foam or array of bubbles that entrap the gas. The foam or bubbles are formed by the permeation of the second reactant added to the formed matrix that includes a reactant. When the two reactants interact, a reaction occurs that liberates gas which is entrapped within the matrix. For example, a matrix has a carbonate catalyst (a reactant) incorporated within it. The formed matrix is then placed in the presence of the second reactant, hydrogen peroxide. A catalytic decomposition of hydrogen peroxide occurs resulting in the liberation of oxygen gas which becomes entrapped as bubbles formed in situ. The hydrogen peroxide reactant is not part of the compounding of the matrix, but it is in the treatment after the formation of the matrix stock.

According to the process, a gelling mixture of at least one cross-linkable biosorbable polymer is prepared. This may be accomplished by creating a solution of a cross-linkable biosorbable polymer or a solution composed of a mixture of cross-linkable biosorbable polymers. The solution is desirably an aqueous solution or a solution where water component is the major component. As an example, a gelling mixture may be prepared by mixing aqueous solutions of gelatin and propylene glycol alginate in the desired ratio. For example, the weight ratio of gelatin to propylene glycol alginate may range from about 1.5:1 to about 6:1. More desirably, the weight ratio of gelatin to propylene glycol alginate may range from about 2:1 to about 5:1. Still more desirably, the weight ratio of gelatin to propylene glycol alginate may range from about 2.5:1 to about 3.5:1.

A catalyst may be introduced into the gelling mixture. For example, the catalyst may be sodium carbonate. The catalyst may be sodium carbonate. However, other catalysts such as other alkali and alkali earth compounds may be used provided they are consistent with the product being biosorbable. In addition, more than one catalyst may be used. For instance, one catalyst may be derived from a group consisting of salts of alkali metals and alkali earth metals and the second catalyst may include, but are not limited to, organic and inorganic chemicals such as cupric chloride, ferric chloride, manganese oxide, sodium iodide and their equivalents. Other catalysts, include, but are not limited to enzymes such as lactoperoxidase and catalase. Desirably, the catalyst is a material that interacts with the second reactant.

A non-gellable polysaccharide, plasticizer and/or a hydration control agent may be added to the gelling mixture. Desirably, the non-gellable polysaccharide is a non-gellable galactomannan macromolecule such a guar gum. A concentration range of guar gum between approximately 0.005 to 53% w/w, preferably between approximately 0.05 to 5% w/w, and most preferably between approximately 0.25 to 1% w/w is generally sufficient. Examples of other suitable non-gellable polysaccharides include lucerne, fenugreek, honey locust bean gum, white clover bean gum, or carob locust bean gum.

The plasticizer(s) may be glycerol and/or water, however, propylene glycol and/or butanol and combinations thereof may also be used. If glycerol is used, a range of between approximately 0.25 to 25% w/w, preferably between 0.5 to 12% w/w, and most preferably between approximately 2.5 to 8% w/w is generally sufficient. The biosorbable matrix may further include a hydration control agent.

The hydration control agent may be an isopropyl alcohol; however, ethanol, glycerol, butanol, and/or propylene glycol and combinations thereof may also be used. A range of isopropyl alcohol of between approximately 0.05 to 5% w/w, preferably between approximately 0.1 to 2.5% w/w and most preferably between approximately 0.25 to 1% w/w is generally sufficient.

The cross-linkable biosorbable polymer of the gelling mixture is then cross-linked to form a water swellable, cross-linked biosorbable polymer network. This may be accomplished by activating a cross-linking agent already present in the gelling mixture, adding or applying a cross-linking agent to the gelling mixture, dehydrating or removing solvent from the gelling mixture, and/or otherwise creating conditions in the gelling mixture that causes cross-linking (e.g., pH, heat, various forms of radiation including electromagnetic radiation and x-rays, ultrasonic energy, microwave energy and the like).

For example, when the gelling mixture is propylene glycol alginate and gelatin, the gelling mixture may be cross-linked by creating alkaline conditions (e.g., pH>8) and dehydrating the gelling mixture. This may be accomplished by adding a base such as, for example, sodium carbonate to the gelling mixture during the initial preparation of the gelling mixture to create alkaline conditions and then dehydrating the gelling mixture to a flexible substrate (i.e., a gel sheet) that can be readily handled. The gel sheet may range in thickness from a few millimeters to 20 millimeters or more. As an example, the alkaline gelling mixture may be cross-linked by pouring into a flat open container to maximize surface area and placing the open contain in a conventional oven at an elevated temperature (e.g., 45 to 65° C.) and dehydrating for 2 to 6 hours until the sheet reaches a consistency similar to "fruit leather" or "fruit roll-up". Fruit leather or fruit roll-up has a gravimetric or weight-based moisture content of about 10 to about 20 percent. Desirably, the matrix is flexible and elastic, and may be a semi-solid scaffold that is permeable to substances such as aqueous fluids, inorganic salts, and dissolved gaseous agents including oxygen. Though not wishing to be bound by any particular theory, it is thought that the substances permeate the matrix through movement via intermolecular spaces among the cross-linked polymer.

A second reactant is then added to the gel sheet. This may be accomplished by immersing the gel sheet in the second reactant, or by spraying, brushing, coating or applying the second reactant. Desirably, the second reactant is hydrogen peroxide. The hydrogen peroxide may be from 5% wt. to 20% or more. Other peroxides may be substituted, including, but not limited to, urea peroxide, sodium peroxide or other peroxy compounds of alkali metal or alkali earth metals. The second reactant preferably is present in aqueous solution or a solution wherein water is major component.

The second reactant is absorbed into the gel sheet and permeates the swellable, (e.g., water-swellable) cross-linked biosorbable polymer matrix. The degree of swelling may be increased by adding a non-gellable polysaccharide such as guar gum and by adding a hydration control agent such as glycerol. By making the cross-linked biosorbable polymer network sufficiently water-swellable, the second reactant (e.g., hydrogen peroxide) may be adequately absorbed into the cross-linked biosorbable polymer network. It has been found that the hydration capacity can be expressed as "water absorption capacity" at 25° C. after an immersion or soak time in distilled water after 3 to 4 hours. Useful levels of hydration capacity may range from about 2 to about 8 grams of water per gram of biosorbable polymer network. For example, the level of water absorption capacity may range from about 3 to about 7 grams of water per gram of biosorbable polymer network. As another example, the level of hydration capacity may range from about 4 to about 6 grams of water per gram of biosorbable polymer network.

According to the process of the present invention, when the second reactant is absorbed and permeates into the cross-linked biosorbable polymer matrix (e.g., cross-linked propylene glycol alginate and gelatin which incorporates a non-gellable polysaccharide), a gas is generated when the catalyst (i.e., the first reactant) reacts with the second reactant. The resulting gas is desirably oxygen gas. The matrix of the present invention forms a foam or array of bubbles that entrap the gas. That is, a plurality of closed cells containing oxygen is generated in the gel sheet by reaction between the catalyst (i.e., the first reactant) and the second reactant. In finished form the gel sheet transforms into a foam sheet.

For example, a cross-linked biosorbable polymer matrix may have a carbonate catalyst (i.e., a first reactant) incorporated within it. The cross-linked biosorbable polymer matrix is then placed in the presence of the second reactant, hydrogen peroxide. A catalytic decomposition of hydrogen peroxide occurs resulting in the liberation of oxygen gas which becomes entrapped as bubbles formed in situ. The hydrogen peroxide reactant is not part of the compounding of the matrix, but it is added after the formation of the matrix stock.

It is contemplated that the process of the present invention may further include the step of heating or adding energy to the gel sheet and second reactant to speed up the reaction incorporating an active agent. One or more active agents may be incorporated at any suitable step in the method. For example, active agents may be added to the gelling mixture prior to cross-linking. Active agents may be added to the cross-linked polymer matrix prior to dehydration or after dehydration. It is contemplated that active agents may be added to the cross-linked polymer matrix after the closed cells are formed.

The present invention also encompasses a method of using an oxygen-delivery wound treatment device. The method of using an oxygen-delivery wound treatment device generally includes the following steps: placing a biosorbable oxygen-delivery wound treatment device composed of an above-described biosorbable matrix for delivering oxygen in a wound or surgical incision site in a mammal; delivering oxygen from the closed cells to the wound or surgical incision site; and leaving the biosorbable oxygen-delivery wound treatment device in the wound or surgical incision site to be resorbed by the mammal. Prior to insertion into the surgical site, the device may be wetted with small quantity of sterile saline solution.

The present invention is further described by the examples which follow. Such examples, however, are not to be construed as limiting in any way either the spirit or the scope of the present invention.

EXAMPLES

All chemicals used in the examples described below were reagent grade unless specified otherwise.

Example 1

Preparation of Bioabsorbable Wound Treatment Device Prototype

The method of making the dressing consisted of four main steps (i) preparation of stock solutions of necessary chemicals (ii) preparation of gelling mixture and (iii) drying the gelling mixture to gel sheet and (iv) finally, transforming the gel sheet into a biosorbable wound treatment device (i.e., a biosorbable foam dressing).

(1). Preparation of Stock Solutions of Gelatin and Sodium Carbonate: 7.20 gram of anhydrous $Na_2CO_3$ (Fisher Scientific) was dissolved in 200 ml de-ionized (DI) water under stirring in a 250 ml Pyrex bottle to prepare stock solution (0.34M). Gelatin (Sigma-Aldrich, Type A) was added to 45 ml DI water in wide mouth glass jar and placed in 50° C. water bath until completely dissolved. The gelatin stock solution (10% w/w) thus made was left fluid by keeping the jar at 50° C. (otherwise it solidifies at room temperature) until ready for use.

(2). Preparation of Gelling Mixture: Weighed quantities of Propylene Glycol Alginate (PGA, Spectrum Chemical, 1.00 gm.) powder and Guar Gum powder (Spectrum Chemical, 0.50 gm.) were transferred to a polypropylene cup (140 ml capacity) and blended to uniformity with the help of a spatula. Next, Isopropanol (IPA, Univar Inc., 1.00 gm.) was pipetted into the dry powder and mixed with a spatula to obtain a paste. To this paste, the following ingredients in that order were added and hand mixed with a spatula.

(a) DI water (44 mL) in aliquots of 4-5 mL water at a time,
(b) Glycerol (VVF Limited, 4.0 g),
c) $Na_2CO_3$ stock solution (0.34M, 9.0 mL),
(d) Gelatin stock solution at 50° C. (40.0 g) to yield a clear to opaque viscous gel mass.

The viscous gel mixture (not cooled) in the cup was poured into a plastic petri-dish (150 mm×15 mm) and left to set to a stiff gel at room temperature for 20-30 minutes. Prior to pouring the gel into the petri-dish, the dish was coated with mineral to aid in the release of set gel. After the set period was over, the gel in the petri dish was transferred to a conventional oven at 55° C. and dehydrated for 4 hours. The dehydrated gel transformed into a gel sheet having consistency of fruit leather as shown in FIG. 1 of the drawings.

Figure 2:
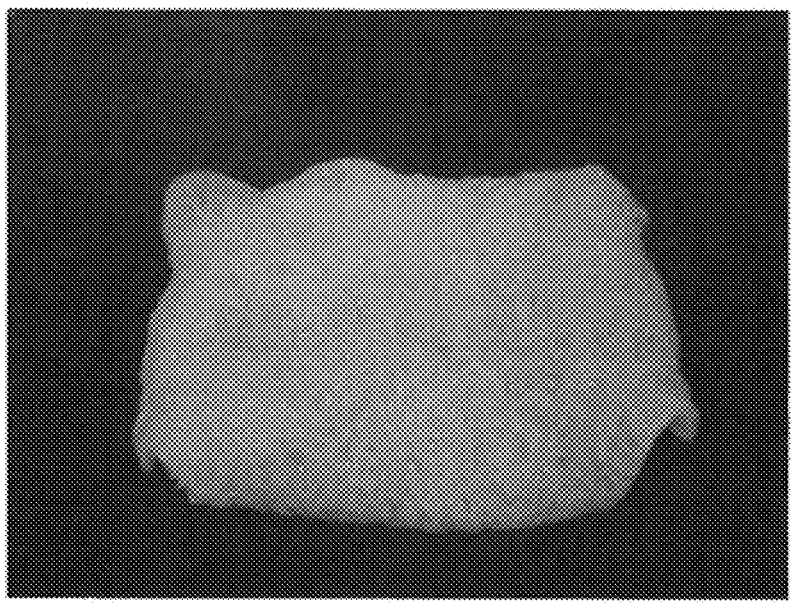
FIG. 2 is a photograph illustrating an exemplary cross-linked biosorbable polymer matrix after formation of closed cells containing a gas.

(3). Preparation of Foam Dressing: The gel sheet from previous step was peeled off from the petri-dish and immersed in 15% w/w hydrogen peroxide solution in a shallow container (Spectrum) for 20 minutes to soak up $H_2O_2$. Excess $H_2O_2$ was rinsed from the wet sheet surface by placing it for few seconds in a second shallow dish filled with DI water. The wet gel sheet was padded down with dry paper towels to remove excess water. The blotted gel sheet was placed on a petri-dish and heated in the microwave oven (Panasonic, Genius Sensor 1250 W) to raise its temperature to 55-60° C. (P8 level for 3 consecutive 10 s cycles). Heating initiated $H_2O_2$ decomposition to $O_2$ gas that was trapped in the soft wet gel sheet. Following the initiation of foaming by microwave heating, the partially foamed sheet was further heated in conventional oven set at 55 C for 15-20 minutes to complete the foaming process, to yield a bioabsorbable closed cell $O_2$ foam sheet dressing. Due to some uneven drying, the foam dressing prototype was warped in various locations (see FIG. 2). To prevent moisture loss, the dressing was stored in a petri dish sealed with Parafilm®.

Example 2

Study of the Effect of Gelatin to PGA Ratio on the Foaming of Biosorbable Gel Sheet The weight ratio of gelatin to PGA in the gelling mixture (4:1 for the gel sheet in Example 1) was varied up to 5:1 and its effect on the dehydrated gel sheet and its subsequent foaming was studied. For the study, the ingredient proportions for making the gel sheet were half of those employed in Example 1 and are listed in Table 1. The gel sheet was made following the method of Example 1 except the petri dish used for gelling and drying was smaller (60 mm×15 mm). Using the smaller petri dish did not alter the thickness of the final dressing as the gelling mixture volume was halved from Example 1. After each gel sheet was soaked in $H_2O_2$ and then foamed, observations of the gel sheet following soaking and the foam sheet were noted in Table 2.

TABLE 1

Amounts of ingredients used in making gel sheets with varying gelatin to PGA ratio

| | Gelatin to PGA Weight ratio | | | |
|---|---|---|---|---|
| | 2:1 | 3:1 | 4:1 | 5:1 |
| PGA | 0.50 g | 0.50 g | 0.50 g | 0.50 g |
| Guar Gum | 0.25 g | 0.25 g | 0.25 g | 0.25 g |

TABLE 1-continued

Amounts of ingredients used in making gel sheets with varying gelatin to PGA ratio

| | Gelatin to PGA Weight ratio | | | |
|---|---|---|---|---|
| | 2:1 | 3:1 | 4:1 | 5:1 |
| IPA | 0.50 g | 0.50 g | 0.50 g | 0.50 g |
| Di water | 22.0 g | 22.0 g | 22.0 g | 22.0 g |
| Glycerol | 2.0 g | 2.0 g | 2.0 g | 2.0 g |
| $Na_2CO_3$ stock solution (0.34M) | 4.5 g | 4.5 g | 4.5 g | 4.5 g |
| Gelatin Solution @40° C. | 20 g 5% w/w (1.0 gram) | 20 g 7.5% w/w (1.5 gram) | 20 g 10% w/w (2.0 gram) | 20 g 12.5% w/w (2.5 gram) |

TABLE 2

Observations regarding gel sheet after $H_2O_2$ soak and conversion to foam sheet in oven

| Gelatin:PGA Wt. ratio | After 20 min soak in 15% w/w $H_2O_2$ | After 20 minute in 55° C. Oven to cause foaming |
|---|---|---|
| 2:1 | The sheet flatter (less warped) due to smaller size hence stronger | Foam sheet was soft and slightly tacky |
| 3:1 | Few $O_2$ bubbles formed in the wet gel sheet | More $O_2$ bubbles than 2:1 ratio foam sheet and bubbles density uniform |
| 4:1 | $O_2$ Bubbles formed in the wet gel sheet | Foam sheet similar to 3:1 experiment, but bubbles were slightly large |
| 5:1 | Large number of $O_2$ bubbles in the wet gel sheet | The foam sheet shrunk. $O_2$ bubbles were small and not uniform |

Example 3

Effect of Soaking on Gel Sheet in Solutions of Varying $H_2O_2$ Concentrations and the Resulting Foam Sheet Following the method of Example 1, a thinner $O_2$ foam sheet dressing was made by halving the amounts of ingredients. Three square pieces of ~1"×1" were cut from the same dressing sheet. Each piece was soaked separately in 3 different solutions at 25° C. containing 5%, 10%, and 15% w/w $H_2O_2$ respectively for a period of 3 minutes. The procedure was repeated by for two additional soak times of 6 minutes and 9 minutes. Observations of the effects on the gel sheet were recorded immediately after soaking and after 10 minutes heat treatment in 55° C. oven.

TABLE 3

Observations of gel sheet after Hydrogen Peroxide Soak

| Soak time | 5% w/w $H_2O_2$ | 10% w/w $H_2O_2$ | 15% w/w $H_2O_2$ |
|---|---|---|---|
| 3 min | Some bubbles, tacky | More small bubbles, tacky | Much more bubbles, tacky |
| 6 min | Some bubbles, tacky | More small bubbles, tacky | Much more bubbles, tacky, and thin |
| 9 min | Some bubbles, tacky | More small bubbles, tacky | Much bubbles, tacky and thin |

TABLE 4

Observations after 10 minutes of heating peroxide soaked gel sheet in 55° C. oven

| | 5% w/w $H_2O_2$ | 10% w/w $H_2O_2$ | 15% w/w $H_2O_2$ |
|---|---|---|---|
| 3 min | Consistent small and large bubbles, not tacky | Mostly small bubbles, but there are pocket of larger bubbles. | Large number of small bubbles forming |
| 6 min | Consistent small and large bubbles, not tacky | Smaller bubbles localize on the center of the dressing | Large bubbles formed, but too much H2O2 soaked in degrading the structural integrity of the foam with time |
| 9 min | More small bubbles and some large bubbles, not tacky | Smaller bubbles localize on the center of the dressing, with larger bubbles on the perimeter | The structure integrity of the foam is damaged due to high absorption of $H_2O_2$ |

Example 4

Effect of Varying % of $H_2O_2$ in Soak Solution Keeping in Soak Period Constant on the Gel Sheet and Resulting Foam Sheet Dressing Four separate gel sheets were made according procedure of Example 1. One sample sheet each was soaked for a period of 20 minutes in the solutions of hydrogen peroxide (Spectrum) with concentrations of 5%, 10%, 15%, and 20% w/w respectively. The hydrated gel sheet was foamed as described in Example 1 and the observations regarding the foam dressings were recorded in Table 5.

TABLE 5

Observations regarding the foam dressings made by soaking in varying $H_2O_2$ solutions

| % w/w Hydrogen Peroxide | Observation after soak | Observation after foam sheet was formed |
|---|---|---|
| 5% | Miniature bubbles formed inside the gel sheet. | The dressing was thin and dry Foaming was uneven |
| 10% | More bubbles formed inside the gel sheet than the 5% $H_2O_2$ soak | Nice appearance. Bubble formation was uniform |
| 15% | More bubble formation inside the dressing than 10% $H_2O_2$ soak | More number of $O_2$ bubbles than 5 or 10% soaked foam |
| 20% | Large number of large size bubbles formed within the gel sheet | Highest number of bubbles formed. The bubbles burst in some areas and were tacky to touch |

Example 5

Effect of Varying the Duration of 15% w/w $H_2O_2$ Soak on the Gel Sheet and the Resulting Foam Sheet Dressing Four gel sheets were made according to procedure in Example 1. Each was soaked in 15% w/w $H_2O_2$ solution but the soak time was varied from 10, 15, 20, and 30 minutes. The gel sheets were observed after soaking and subsequent conversion to a foam sheet dressing. The observations are noted in Table 6 below.

TABLE 6

Observations regarding gel sheets and resulting foam sheets obtained from varying soak times in 15% w/w $H_2O_2$

| Time | Observation after soak | Observation regarding foam sheet |
|---|---|---|
| 10 min | The gel sheet had many bubbles already formed | Foam dressing fine, but it was somewhat dry |
| 15 min | More bubbles formed than above | Dressing was better than above and larger in size than above |
| 20 min | More bubbles formed than above | Dressing was the best of all. Very uniform bubbles and very evenly distributed than above |
| 30 min | Lots of bubbles formed in the gel sheet making it fragile | Bubble burst when during microwave heating. Dressing was very tacky |

Example 6

Hydration Capacity of Gel Sheet

Following the method of Example 1, one gel sheet was prepared. Three pieces (~1"×1") of the gel sheet were cut and labeled samples—A, B, and C. The mass for each sample was initially measured. The sample pieces dressing was immersed in Di water at 25° C. for 3 different durations—30 minutes, 3 hours, and 24 hours. At each time point, the piece was removed, blotted dry with paper towel, and weighed. From its weight before and after hydration, the hydration capacity as % of initial was calculated. The data are listed in Table 7.

TABLE 7

Hydration capacity of the gel sheet made in Example 1

| | Time of Soak | | |
|---|---|---|---|
| | 0.5 hour | 3 hours | 24 hours |
| Sample A | 220% | 359% | 428% |
| Sample B | 344% | 407% | 467% |
| Sample C | 244% | 314% | 338% |
| Average % (±Stddev) | 269% (±65%) | 360% (±46%) | 411% (±66%) |

Hydration capacity = 100 × (Final weight − Initial weight)/Initial weight

Example 7

$O_2$ Flux Measurement from Oxygen Foam Dressing of Example 1

Figure 3:
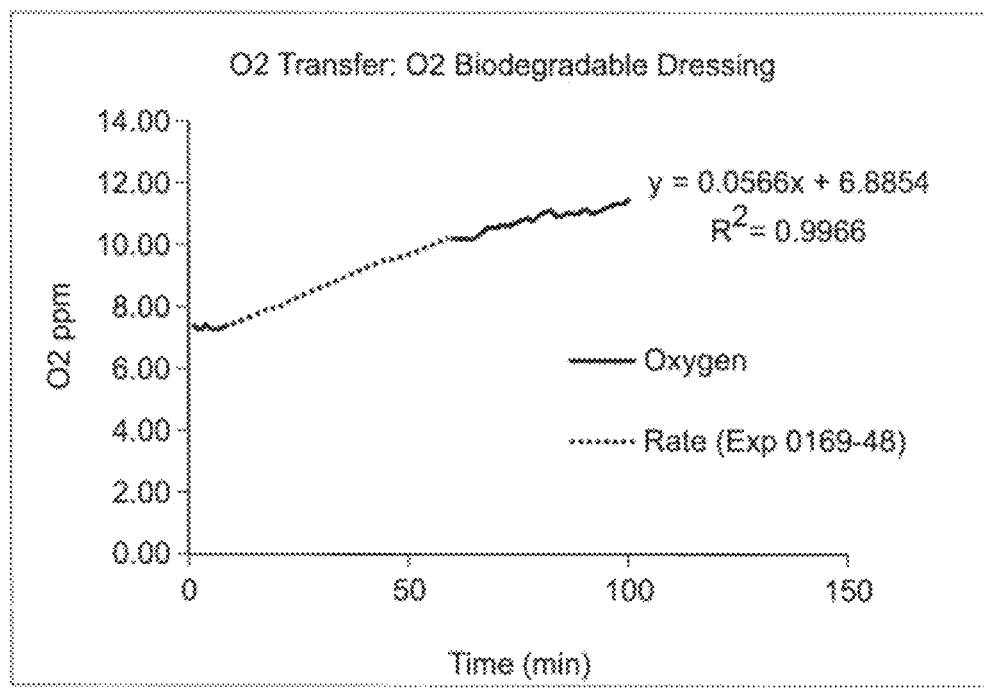
FIG. 3 is an illustration of a plot of oxygen ($O_2$) uptake by saline in a Franz cell demonstrating the delivery of oxygen from an exemplary biosorbable wound treatment device.

The flux of dissolved oxygen from the $O_2$ foam dressing made in Example 1 was measured as follows. A circular oxygen dressing with 30 mm diameter was cut from the foam dressing and wetted with ~1 mL de-ionized water. The wet foam piece was placed on top of a PE membrane (~25 mm thick) of a Franz cell and held in place to ensure intimate contact with the membrane by a circular weighty plastic top. The membrane acted as a flexible wall of the Franz cell that was filled with air saturated saline solution. The cell was fitted with a dissolved $O_2$ measuring probe (Foxy® from Ocean Optics, FL). The dissolve $O_2$ probe allowed the monitoring of $O_2$ content of the saline solution in ppm over time. Immediately after the dressing piece was placed in contact with the PE membrane, the $O_2$ concentration in saline solution was monitored. After an initial time lag of 5 minutes, the $O_2$ concentration began to increase linearly with time for the next 60 to 90 minutes (see FIG. 3). Using the linear slope value, the $O_2$ flux ($\mu g/cm^2/min$) was calculated as ~0.13 $\mu g/cm^2/min$ from a simple mathematical model.

Prophetic Examples

Example 1

Hyaluronate Based $O_2$ Foam Dressing 0.36 gm. of Sodium hyaluronate (MW of at least $1e^6$) is dissolved in 4.74 gm of 0.2M Sodium Hydroxide in a dram vial (20 ml capacity) with a small magnetic stirrer. 0.36 gm. of Divinyl sulfone is dissolved in the solution (HA to DVA weight ratio 1:1). Finally, 0.54 gm. glycerol is added. The mixture is poured into a small plastic petri-dish that is then covered with a lid. The petri-dish surface is rubbed with mineral oil prior to pouring the hyaluronate mixture. After about 2 hours at room temperature (~25° C.), the contents of the petri-dish are turned into a gel. The small round gel sheet is transferred to a nylon mesh and left in an oven set to 55° C. for 2-4-h to remove moisture from the sheet. After roughly ~75% weight loss, the gel sheet is turned into a material with the consistency of fruit leather.

The HA gel sheet made above is soaked briefly (less than 5 minutes) in a 10-30% wt. aqueous solution of $H_2O_2$. The soaked sheet is blotted dry on a paper and heated in microwave oven to initiate $H_2O_2$ decomposition to $O_2$ and cause foaming. If needed the microwaved gel sheet can be then transferred to a conventional oven set at 55 C to complete the $H_2O_2$ decomposition resulting in a dry to touch $O_2$ foam sheet. The hyaluronate based $O_2$ foam dressing is expected to be biosorbable as hyaluronate has been known to biodegrade in vivo enzymatically.

Example 2

$O_2$ Foam Dressing Based on Hyaluronate and Collagen

A solution of hyaluronate and collagen with divinyl sulfone as cross-linking agent is prepared in a manner described in Example 15 of the U.S. Pat. No. 4,582,865 except that the amounts are doubled. To this solution, 1.2 ml of glycerol is added and blended in. The mixture is treated as in the Prophetic Example 1 above to obtain a biosorbable $O_2$ foam dressing.

Example 3

$O_2$ Foam Dressing Based on Poly(Ethylene Glycol Maleate Citrate)

The base polymer is first prepared as described in the material and methods section of the article "Citric acid derived in situ cross-linkable biodegradable polymers for cell delivery" by Gyawali D et al., BioMaterials (2010), doi: 10.1016/j.biomaterials.2010.08.022. A 30% w/v solution of the resulting polymer (purified) is cross-linked with acrylic acid as cross-linking agent at 3% w/v concentration by redox initiator system—Ammonium persulfate and Tetramethyl-ethylenediamine as described therein. Prior to initiating polymerization, glycerol and guar gum are dissolved in so that their concentration in the mixture is ~10% and 1% w/w respectively. The viscous mixture is poured in an oiled petri-dish and polymerization is carried out at room temperature for 2 hours to obtain a gel sheet. Longer period of polymerization than described in the article ensures complete conversion of the vinyl units and thus minimizing sol formation. The gel sheet is dehydrated as in Prophetic Example 1. It is then rehydrated with 0.5M sodium carbonate solution for 15 minutes and dehydrated again. Finally, the gel sheet is soaked in 10-30% wt. $H_2O_2$ solution for 5-10 min, blotted dry, briefly microwaved (<5 minutes in small 10-15 seconds exposures as needed) and transferred to the oven set to 55° C. to complete the foaming process. After drying for about 45 min to 1 hour in the oven, $O_2$ foam dressing is obtained.

Example 4

$O_2$ Foam Dressing Based on Poly(Caprolactone Diol-Co-Polypropylene Fumarate-Co-Ethylene Glycol)

The base polymer is prepared by following the procedure described in the materials and methods section 2.1 of the article by Krishna L and Jayabalan M in J. Mater. Sci. Mater. Med. Vol. 20, pS115-122 (2009). The base polymer is cross-linked to an insoluble hydrogel, with acrylamide as the cross-linking agent. The recipe disclosed in the Table 2 of the article is followed. In addition to the listed ingredients, glycerol (0.25 g) and sodium carbonate (0.1 to 0.15 g) are added to the polymerization mixture and polymerized to a hydrogel (Note the inorganic compound must be completely dissolved in the mixture and small amount of water (over the listed amount) may be added to aid its dissolution. The resulting hydrogel is then dehydrated to the consistency of fruit leather in an oven at 55° C. for 1-2 hours, periodically observing the hydrogel material for the desired texture, feel and appearance.

The dehydrated hydrogel is removed for the oven and cooled to room temperature. It is then immersed in a shallow dish filled with ~10 to 15% w/w aqueous hydrogen peroxide at 25 C for 20 minutes or less. The swollen hydrogel is carefully transferred to a nylon mesh and re-placed in the oven at 55° C. from 0.25 hour to 1 hour. As the hydrogel is heated to 55° C., the in-situ decomposition by sodium carbonate to gaseous oxygen ensues, resulting in transformation of the hydrogel to a foamy material. The foam dressing obtained is closed cell foam filled with pure oxygen gas, flexible and is expected to be biosorbable. Please note the use of acrylamide as cross-linking agent in this example is for illustrative purposes and non-limiting. Those ordinarily skilled in the art know of other cross-linking agents that have two vinyl groups that are suitable in making the biosorbable $O_2$ foam dressing of the present invention. Such agents, it is preferred, break down in vivo to harmless non-toxic products along with the base polymer.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:
1. A biosorbable oxygen-delivery wound treatment device comprising a biosorbable matrix for delivering oxygen, the matrix comprising:
 a water swellable, cross-linked biosorbable polymer network comprising gelatin and propylene glycol alginate, wherein the weight ratio of gelatin to propylene glycol alginate ranges from about 1.5:1 to about 6:1;
 a plurality of gas-permeable, elastic, closed cells defined by the cross-linked biosorbable polymer network, the closed cells resulting from a reaction between a catalyst and a second reactant; and
 deliverable oxygen within the elastic closed cells, such that when the device is used to treat a wound, oxygen is delivered from the closed cells.
2. The device of claim 1, wherein the biosorbable polymer network further comprises a biosorbable polymer selected from hyaluronic acid and hyaluronic acid derivatives, alginic acid and alginic acid derivatives, collagen, chitosan, chitin, starch derivatives, gums, citric acid based polymers, lactic acid and glycolic acid based polymers, poly(aspartates), poly (orthoesters), poly (phosphazenes), poly(anhydrides), poly (phosphoesters), polyalkylene glycol based polymers, and combinations thereof.
3. The device of claim 1, wherein the biosorbable polymer network further comprises a non-gellable polysaccharide.
4. The device of claim 1, wherein the second reactant is a peroxide.
5. The device of claim 1, wherein the catalyst is sodium carbonate.
6. The device of claim 1, wherein the biosorbable matrix further comprises an active agent.
7. The device of claim 1, wherein the biosorbable matrix further comprises a stranded configuration.
8. The device of claim 1, wherein the second reactant is a peroxide and the catalyst is sodium carbonate.
9. A process for making a biosorbable oxygen-delivery wound treatment device comprising a biosorbable matrix for delivering oxygen, the method comprising the steps of:
 providing a gelling mixture of at least one cross-linkable biosorbable polymer and a catalyst, wherein the at least one cross-linkable biosorbable polymer of the gelling mixture comprises gelatin and propylene glycol alginate, wherein the weight ratio of gelatin to propylene glycol alginate ranges from about 1.5:1 to about 6:1;
 cross-linking the biosorbable polymer of the gelling mixture to form a water swellable, cross-linked biosorbable polymer network;
 drying the gelling mixture to a gel sheet;
 adding a second reactant to the gel sheet; and
 generating a plurality of closed cells containing oxygen in the gel sheet by reacting the catalyst and the second reactant.
10. The process of claim 9, wherein cross-linking and drying are accomplished in the same step.
11. The process of claim 10, wherein cross-linking is accomplished by creating alkaline conditions in the gelling mixture.
12. The process of claim 9, wherein the second reactant is a peroxide.
13. The process of claim 9, wherein the catalyst is sodium carbonate.

14. The process of claim 11, wherein cross-linking is accomplished by creating alkaline conditions in the gelling mixture utilizing sodium carbonate and further wherein the catalyst is sodium carbonate.

15. The process of claim 9, further comprising the step of incorporating an active agent.

16. A method of using an oxygen-delivery wound treatment device comprising:
- placing a biosorbable oxygen-delivery wound treatment device comprising a biosorbable matrix for delivering oxygen in a wound or surgical incision site in a mammal, the biosorbable matrix comprising:
- a swellable, cross-linked biosorbable polymer network comprising gelation and propylene glycol alginate, wherein the weight ratio of gleation to propylene glycol alginate ranges from about 1.5:1 to about 6:1;
- a plurality of gas-permeable, elastic, closed cells defined by the cross-linked biosorbable polymer network, the closed cells generated by reaction between a catalyst and a second reactant; and
- deliverable oxygen within the elastic closed cells, delivering oxygen from the closed cells to the wound or surgical incision site; and leaving the biosorbable oxygen-delivery wound treatment device in the wound or surgical incision site to be resorbed by the mammal.

17. The method of claim 16, wherein the biosorbable matrix further comprises an active agent and an active agent is delivered to the wound or surgical incision site.

\* \* \* \* \*